(12) United States Patent
Gralla et al.

(10) Patent No.: US 8,791,276 B2
(45) Date of Patent: Jul. 29, 2014

(54) PROCESS FOR THE PREPARATION AND ISOLATION OF 2-SUBSTITUTED TETRAHYDROPYRANOLS

(75) Inventors: Gabriele Gralla, Mannheim (DE); Karl Beck, Östringen (DE); Margarethe Klos, Mannheim (DE); Ulrich Griesbach, Mannheim (DE)

(73) Assignee: BASF SE, Ludwigshafen (DE)

( * ) Notice: Subject to any disclaimer, the term of this patent is extended or adjusted under 35 U.S.C. 154(b) by 226 days.

(21) Appl. No.: 13/157,732

(22) Filed: Jun. 10, 2011

(65) Prior Publication Data

US 2011/0306779 A1    Dec. 15, 2011

Related U.S. Application Data

(60) Provisional application No. 61/353,218, filed on Jun. 10, 2010.

(51) Int. Cl.
*C07D 309/10* (2006.01)

(52) U.S. Cl.
USPC ........................................ 549/423

(58) Field of Classification Search
USPC ................................. 549/423, 416
See application file for complete search history.

(56) References Cited

U.S. PATENT DOCUMENTS

| 2,271,134 | A | 1/1942 | Will et al. |
| 4,230,533 | A | 10/1980 | Giroux |
| 5,530,127 | A | 6/1996 | Reif et al. |
| 2011/0295024 | A1 | 12/2011 | Gralla et al. |
| 2011/0306779 | A1 | 12/2011 | Gralla et al. |
| 2012/0059177 | A1 | 3/2012 | Gralla et al. |

FOREIGN PATENT DOCUMENTS

| DE | 10223971 A1 | 12/2003 |
| EP | 122 367 A2 | 10/1984 |
| EP | 126 288 A2 | 11/1984 |
| EP | 133 510 A1 | 2/1985 |
| EP | 640 367 A1 | 3/1995 |
| EP | 0696572 A1 | 2/1996 |
| EP | 1493737 A1 | 1/2005 |
| EP | 1516879 A1 | 3/2005 |
| JP | 2007-154069 A | 6/2007 |
| JP | 2007-154609 A * | 6/2007 |
| SU | 825528 A1 | 4/1981 |
| SU | 828828 A1 * | 4/1981 |
| WO | WO-2010133473 A1 | 11/2010 |

OTHER PUBLICATIONS

Gevorkyan et al (II), Chemistry of Heterocyclic Compounds, No. 12, p. 1240-1242 (1982).*
Ennenbach et al, www.digitalrefining.com/article/1000630 (Oct. 1980).*
De Silva, Essentials of Ion Exchange, presented at the 25th Annual WQA Conference (Mar. 17, 1999) (from the Internet).*
Tetrahedron Letters No. 51, 1970, pp. 4507-4508.
Chemistry of Heterocyclic Compounds, 1990, pp. 1107-1109.
Alexandra Macedo, J. Braz. Chem. Soc., vol. 21, 2010, pp. 1563-1571.
Definition of Ion Exchange Resins, from The Great Soviet Encyclopedia (1979) (from the Internet).
Ibatullin, Chemistry of Heterocyclic Compounds, vol. 25, 1989, pp. 1107-1109.
Pankaj Gupta, Helvetica Chimica Acta, vol. 90, 2007, pp. 196-204.
Tetrahedron Letters No. 51, pp. 4507-4508, 1970.
Thomson Scientific, London, 2007-564955.
Thomson Scientific, London, 1982-11549E.

* cited by examiner

*Primary Examiner* — Kristin Vajda
(74) *Attorney, Agent, or Firm* — Drinker Biddle & Reath LLP

(57) ABSTRACT

Process for the preparation of 2-substituted 4-hydroxy-4-methyltetrahydropyrans of the formula (I)

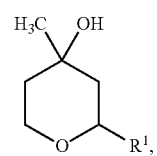

(I)

where the radical
$R^1$ is a straight-chain or branched alkyl or alkenyl radical having 1 to 12 carbon atoms, an optionally alkyl-substituted cycloalkyl radical having in total 3 to 12 carbon atoms or an optionally alkyl- and/or alkoxy-substituted aryl radical having in total 6 to 12 carbon atoms,
comprising the reaction of 3-methylbut-3-en-1-ol of the formula (II)

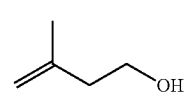

(II)

with an aldehyde of the formula (III)

$R^1$—CHO    (III), where the radical $R^1$ has the same meaning as in formula (I) and
where the reaction is carried out in the presence of water and in the presence of a strongly acidic cation exchanger, and then the isolation and/or the distillative separation is carried out in a dividing wall column or in an interconnection of (at least) two distillation columns in the form of a thermal coupling and one or more side take-off points at an absolute operating pressure of up to 500 mbar.

23 Claims, No Drawings

PROCESS FOR THE PREPARATION AND ISOLATION OF 2-SUBSTITUTED TETRAHYDROPYRANOLS

CROSS-REFERENCE TO RELATED APPLICATIONS

This Application claims the benefit of U.S. Provisional Application 61/353,218 filed on Jun. 10, 2010 which is incorporated by reference.

BACKGROUND OF THE INVENTION

The present invention relates to a process for the preparation and isolation of 2-substituted 4-hydroxy-4-methyltetrahydropyranols by reacting 3-methylbut-3-en-1-ol (isoprenol) with the corresponding aldehydes in the presence of a strongly acidic cation exchanger and subsequent isolation or distillative separation in a dividing wall column or in an interconnection of two distillation columns in the form of a thermal coupling. Specifically, the present invention relates to a corresponding process for the preparation and isolation of 2-isobutyl-4-hydroxy-4-methyltetrahydropyran by reacting isoprenol with isovaleraldehyde and subsequent distillative separation in a dividing wall column or in an interconnection of two distillation columns in the form of a thermal coupling.

Tetrahedron Letters No. 51, pages 4507-4508, 1970 describes the reaction of 3-alken-1-ols with aldehydes and their use for producing the aroma chemicals rose oxide and dihydrorose oxide. Also mentioned here is the reaction of 3-methylbutanal with isoprenol under acidic conditions.

Chemistry of Heterocyclic Compounds, pages 1107-1109, 1990 describes the condensation of isoprenol with various aldehydes and ketones to give the corresponding di- and tetrahydropyrans in the presence of silica gel or $Al_2O_3$ under solvent-free conditions. Pyranols are obtained here only to a low degree when using $Al_2O_3$.

SU 825 528 discloses a process for the preparation of di- and tetrahydropyrans and tetrahydropyranols by reacting 2-methylbuten-1-ol-4 (isoprenol) with aldehydes or ketones in the presence of an acidic catalyst, where the acidic catalyst is used in an amount of from 0.0001 to 0.01% by weight, based on the amount of isoprenol, and the reaction is carried out at a temperature of from 0 to 25° C. in an organic solvent. The catalysts specified are the ion exchange resin KU-2 (sulfonated polystyrene resin), para-toluenesulfonic acid, sulfuric acid, phosphoric acid or perchloric acid. By way of example, the reaction of isoprenol with isobutyraldehyde in the presence of KU-2, inter alia, is described.

EP 1 493 737 A1 discloses a process for the preparation of mixtures of ethylenically unsaturated 4-methyl- and 4-methylenepyrans and the corresponding 4-hydroxypyrans by reacting the corresponding aldehydes with isoprenol, where the reaction is initiated in a reaction system in which the molar ratio of aldehyde to isoprenol is greater than 1, i.e. the aldehyde is used in excess. Moreover, the document discloses the subsequent dehydrogenation of said mixtures to give the desired ethylenically unsaturated pyrans. Suitable catalysts specified for the first reaction step are mineral acids, such as hydrochloric acid or sulfuric acid, but preferably methanesulfonic acid or para-toluenesulfonic acid.

EP 1 516 879 A1 discloses a process for the preparation of ethylenically unsaturated 4-methyl- and 4-methylenepyrans by reacting a corresponding aldehyde with isoprenol under dehydrogenating conditions, where the amount of water in the reactor is up to 0.25% by weight, while the conversion of the starting compound used in deficit is less than 50%. The catalysts specified as being suitable for this are likewise mineral acids, such as hydrochloric acid or sulfuric acid, but preferably methanesulfonic acid or para-toluenesulfonic acid.

JP 2007-154069 relates to 2-substituted 4-hydroxy-4-methyltetrahydropyranols with a content of the cis-diastereomer of from 70 to 95% by weight. Moreover, the document discloses a process for the preparation of same, by reacting isoprenol with a corresponding aldehyde in the presence of an aqueous solution of an acidic catalyst. Here, the reaction has to be carried out at a concentration of the aqueous catalyst solution either in the range from 1 to 10% by weight at a temperature of from 0 to 100° C., or in the region of 10% by weight or above at a temperature of from 0 to 30° C. The possible acidic catalysts mentioned are generally also ion exchange resins.

It is known, for isolating multicomponent systems by distillation, to use e.g. a dividing wall column, i.e. a distillation column with lateral feed positioned between top and bottom and a dividing device in the feed section extending in the longitudinal direction of the column for preventing crossmixing of vapors and/or condensate. However, dividing wall columns have hitherto not been used for separating stereoisomeric alcohols of the formula (I), which usually have a low boiling point difference. The object of the invention is to indicate a process for the preparation and isolation of 2-substituted tetrahydropyranols with which, generally, products with very low boiling point differences can be isolated in the purest form possible from a crude mixture with a low capital and energy requirement.

Distillation columns which comprise a dividing wall are known per se and described e.g. in U.S. Pat. No. 2,271,134, U.S. Pat. No. 4,230,533, EP-A 122 367, EP-A 126 288, EPA 133 510, Chem. Eng. Technol. 10 (1987) 92-98; Chem.-Ing.-Techn. 61 (1989) No. 1, 16-25; Gas Separation and Purification 4 (1990) 109 114; Process Engineering 2 (1993) 33-34; Trans IChemE (1994) Part A 639 644 and Chemical Engineering 7 (1997) 72-76. The dividing wall can be integrated into the column in a fixed manner, e.g. welded in, or else it is attached in the column in a removable manner, e.g. inserted.

The removable fixing offers advantages, such as greater flexibility, simpler packing of the column with internals and low capital costs.

Starting from this prior art, the object of the present invention was to provide a process for the preparation and isolation of 2-substituted 4-hydroxy-4-methyltetrahydropyrans, specifically 2-isobutyl-4-hydroxy-4-methyltetrahydropyran, which makes the desired compounds accessible as far as possible starting from readily available, inexpensive starting materials, using readily available, inexpensive reagents in an operationally advantageous manner, on an industrial scale, in a high yield, in a high diastereomer excess, with the lowest possible formation of undesired by-products that have to be disposed of, in extremely high purity and with as far as possible advantageous olfactory properties.

BRIEF SUMMARY OF THE INVENTION

Surprisingly, the object was achieved according to the invention through the provision of a process for the preparation of 2-substituted 4-hydroxy-4-methyltetrahydropyrans of the formula (I)

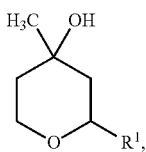

where the radical
R¹ is a straight-chain or branched alkyl or alkenyl radical having 1 to 12 carbon atoms, an optionally alkyl-substituted cycloalkyl radical having in total 3 to 12 carbon atoms or an optionally alkyl- and/or alkoxy-substituted aryl radical having in total 6 to 12 carbon atoms,
comprising the reaction of 3-methylbut-3-en-1-ol of the formula (II)

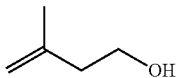

with an aldehyde of the formula (III)

where the radical R¹ has the same meaning as in formula (I) and
where the reaction is carried out in the presence of water and in the presence of a strongly acidic cation exchanger, and then the distillative separation is carried out in a dividing wall column or in an interconnection of at least two distillation columns in the form of a thermal coupling and one or more side take-off points at an absolute operating pressure of up to 500 mbar.

DETAILED DESCRIPTION OF THE INVENTION

For specific applications in the field of aroma or synthesis chemistry, it may be desirable to be able to use the diastereomers separated off by distillation in as pure or enriched a form as possible.

Suitable starting materials for carrying out the process according to the invention are 3-methylbut-3-en-1-ol (isoprenol) of the formula (II),

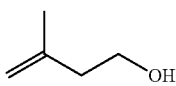

which is readily accessible by known processes from isobutene and formaldehyde on any scale and is commercially readily available. No particular requirements are placed on the purity, grade or preparation process of the isoprenol to be used according to the invention. It can be used as starting material in the course of the process according to the invention in standard commercial grade and purity with good success. Preference is given to using isoprenol which has a purity of 90% by weight or above, particularly preferably one with a purity of from 95 to 100% by weight and very particularly preferably one with a purity of from 97 to 99.9% by weight or even more preferably 98 to 99.8% by weight.

A further suitable starting material for carrying out the process according to the invention is an aldehyde of the formula (III)

where the radical R¹ is a straight-chain or branched alkyl or alkenyl radical having 1 to 12 carbon atoms, an optionally alkyl-substituted cycloalkyl radical having in total 3 to 12 carbon atoms or an optionally alkyl- and/or alkoxy-substituted aryl radical having in total 6 to 12 carbon atoms. Here, the term alkenyl radical is to be understood as meaning a hydrocarbon radical which, besides single bonds, also has one or more, preferably 1 to 3, particularly preferably 1 or 2 and very particularly preferably one, ethylenic double bond.

An alkyl substituent is preferably to be understood as meaning one which has 1 to 6 carbon atoms, such as, for example, methyl, ethyl, n-propyl, isopropyl, n-butyl, sec-butyl, tert-butyl, n-pentyl or n-hexyl, preferably methyl, ethyl, n-propyl, isopropyl, isobutyl.

An alkoxy substituent is preferably to be understood as meaning one which has 1 to 6 carbon atoms, particularly preferably 1 to 3 carbon atoms, such as, for example, methoxy, ethoxy, n-propyloxy, isopropyloxy.

Aldehydes of the formula (III) preferred according to the invention are those in which the radical R¹ is a straight-chain or branched alkyl or alkenyl radical having 1 to 12 carbon atoms, or an optionally alkyl- and/or alkoxy-substituted aryl radical having in total 6 to 12 carbon atoms. According to the invention, very particularly preferred aldehydes of the formula (III) are those in which the radical R¹ is a straight-chain or branched alkyl or alkenyl radical having 1 to 12 carbon atoms or preferably having 1 to 6 carbon atoms, or is an aryl radical having in total 6 carbon atoms, i.e. is phenyl. Particularly preferred aldehydes of the formula (III) are those in which the radical R¹ is a straight-chain or branched alkyl or alkenyl radical having 1 to 12 carbon atoms, very particularly preferably having 1 to 6 carbon atoms. According to the invention, preferred meanings for the radical R¹ are therefore, for example, methyl, ethyl, n-propyl, isopropyl, n-butyl, isobutyl, n-pentyl, n-hexyl, n-heptyl, preferably methyl, ethyl, n-propyl, isopropyl, n-butyl, isobutyl, very particularly preferably isobutyl. As aldehydes of the formula (III) accordingly to be used preferably according to the invention, the following may be mentioned: acetaldehyde, valeraldehyde, isovaleraldehyde, pentanal, hexanal, heptanal, benzaldehyde, citral, citronellal. Aldehydes of the formula (III) to be used very particularly preferably according to the invention are therefore isovaleraldehyde and benzaldehyde, in particular isovaleraldehyde.

Within the context of one preferred embodiment, the present invention therefore relates to a process for the preparation and isolation of 2-isobutyl-4-hydroxy-4-methyltetrahydropyran of the formula (Ia)

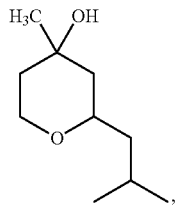

comprising the reaction of 3-methylbut-3-en-1-ol of the formula (II) with isovaleraldehyde of the formula (IIIa)

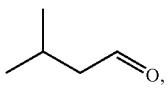
(IIIa)

where the reaction is carried out in the presence of water and in the presence of a strongly acidic cation exchanger, and then the isolation is carried out in a dividing wall column or in an interconnection of two distillation columns in the form of a thermal coupling and one or more side take-off points at an absolute operating pressure of from 3 to 200 mbar.

Within the context of a further, likewise preferred embodiment, the present invention relates to a process for the preparation and isolation of 2-phenyl-4-hydroxy-4-methyltetrahydropyran of the formula (Ib)

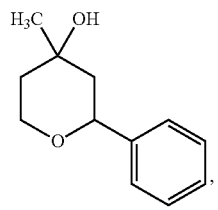
(Ib)

comprising the reaction of 3-methylbut-3-en-1-ol of the formula (II) with benzaldehyde, where the reaction is carried out in the presence of water and in the presence of a strongly acidic cation exchanger, and then the distillative separation is carried out in a dividing wall column or in an interconnection of two distillation columns in the form of a thermal coupling and one or more side take-off points at an absolute operating pressure of from 3 to 200 mbar.

The starting materials isoprenol and the aldehyde of the formula (III) selected in each case to be used in the course of the process according to the invention can be reacted together in various quantitative ratios. Thus, it is possible to use one of the two starting materials in excess, in which case the level of the selected excess should vary within operationally and economically advantageous limits, but otherwise can in principle be freely chosen. Following the stoichiometry of the reaction according to the invention of isoprenol with the selected aldehyde of the formula (III), isoprenol and the aldehyde of the formula (III), preferably isovaleraldehyde, are used in a molar ratio in the range from 1:2 to 2:1, corresponding to a two-fold molar excess of one of the starting materials. Within the context of one preferred embodiment, the process according to the invention is carried out in such a way that isoprenol and the aldehyde of the formula (III) are used in a molar ratio of from 0.7:1 to 2:1. The process according to the invention is particularly preferably carried out in such a way that isoprenol and the aldehyde of the formula (III) are used in a molar ratio of from 1:1 to 2:1. The process according to the invention is particularly preferably carried out in such a way that isoprenol and the aldehyde of the formula (III) are used in a molar ratio of from 1:1 to 1.5:1.

The reaction of isoprenol with the selected aldehyde of the formula (III), preferably with isovaleraldehyde, that is to be carried out in the course of the process according to the invention for the preparation of the 2-substituted 4-hydroxy-4-methyltetrahydropyrans of the formula (I), preferably for the preparation of 2-isobutyl-4-hydroxy-4-methyltetrahydropyran of the formula (Ia), is carried out in the presence of water. This means that, besides isoprenol, the aldehyde of the formula (III) and the selected strongly acidic cation exchanger, water is also added to the reaction mixture. In addition, the reaction mixture can also comprise small amounts of water which can be released by the dehydration of the desired process product of the formula (I) which possibly takes place as an undesired secondary reaction.

The reaction of the isoprenol with the selected aldehyde of the formula (III) is usually carried out in the presence of about at least 10 mol % of water, where the amount of water refers to the amount of the starting material isoprenol used, optionally in deficit, or to the aldehyde of the formula (III), or, in the case of the equimolar reaction of the two starting materials, to the quantitative amount of one of the two.

Above the stated value, the amount of water can be freely chosen and is limited only by processing or cost aspects, if at all, and can be used perfectly well in a large excess, for example in 10- to 100-fold excess or even more. Preferably, a mixture of isoprenol and the selected aldehyde of the formula (III), preferably isovaleraldehyde, is prepared with the selected amount of water such that the added water remains dissolved in the mixture of isoprenol and the selected aldehyde, i.e. no two-phase system is present.

Usually, in the course of the process according to the invention, the starting materials isoprenol and the selected aldehyde of the formula (III) are reacted in the presence of at least 25 mol %, preferably of at least 50 mol %, even more preferably of at least 75 and even more preferably of at least 90 to about 1000 mol %, of water, where the amount of water refers to the amount of the starting material isoprenol used, optionally in deficit, or to the aldehyde of the formula (III), or, in the case of the equimolar reaction of the two starting materials, to the quantitative amount of one of the two.

Within the context of one preferred embodiment, the reaction to be carried out according to the invention is carried out such that it is carried out in the presence of an at least equimolar amount of water, where the amount of water refers to the amount of starting material isoprenol used, optionally in deficit, or to the aldehyde of the formula (III), or, in the case of the equimolar reaction of the two starting materials, to the quantitative amount of one of the two. Consequently, the reaction according to the invention of isoprenol with the selected aldehyde of the formula (III) is preferably carried out in the presence of from 100 to 250 mol %, particularly preferably 100 to 230 mol %, even more preferably 100 to 200 mol % and most preferably in the presence of from 100 to 180 mol %, of water, where the amount of water refers to the amount of the starting material isoprenol used, optionally in deficit, or to the aldehyde of the formula (III), or, in the case of the equimolar reaction of the two starting materials, to the quantitative amount of one of the two.

The specified starting materials, i.e. isoprenol and the aldehyde selected in each case and the water to be used in the above amount can be brought into contact with one another or be mixed in any desired order. Usually, a mixture of isoprenol and the selected aldehyde of the formula (III) is prepared with the selected amount of water and this mixture is used in the course of the reaction to be carried out according to the invention.

The reaction of isoprenol with the selected aldehyde of the formula (III) to be carried out in the course of the process according to the invention for preparing the desired 2-substituted 4-hydroxy-4-methyltetrahydropyrans of the formula (I) is carried out in the presence of a strongly acidic cation exchanger. Within the context of the present invention, the term strongly acidic cation exchanger is to be understood as meaning those cation exchangers in the $H^+$ form which have strongly acidic groups, usually sulfonic acid groups, whose matrix may be gel-like or macroporous.

One preferred embodiment of the process according to the invention is accordingly one in which a strongly acidic cation exchanger having or comprising sulfonic acid groups is used.

Strongly acidic cation exchangers are in particular ion exchange resins in the H(+) form. Examples of such are, for example:

strongly acidic ion exchangers (such as e.g. Amberlyst, Amberlite, Dowex, Lewatit, Purolite, Serdolit), which are based on polystyrene and which comprise copolymers of styrene and divinylbenzene as carrier matrix with sulfonic acid groups in H(+) form, ion exchanger groups functionalized with sulfonic acid groups (—SO$_3$H).

The ion exchangers differ in the structure of their polymer backbones, and a distinction is made between gel-like and macroporous resins. The strongly acidic ion exchange resins are generally regenerated using hydrochloric acid and/or sulfuric acid.

Nafion® is perfluorinated ion exchange materials consisting of fluorocarbon base chains and perfluorinated side chains which comprise sulfonic acid groups. The resins are prepared by a copolymerization of perfluorinated, terminally unsaturated and sulfonylfluoride-functionalized ethoxylates with perfluoroethene. Nafion® belongs to the gel-like ion exchange resins. An example of such a perfluorinated polymeric ion exchange resin which may be mentioned is Nafion® NR-50.

A particularly preferred embodiment of the process according to the invention is one in which at least one strongly acidic cation exchanger is used in the H(+) form, where the ion exchanger comprises a polymer backbone having sulfonic acid groups and is either gel-like or comprises macroporous resins.

A very particularly preferred embodiment of the process according to the invention is one in which the ion exchanger is based on a polystyrene backbone with sulfonic acid groups or on a perfluorinated ion exchange resin with sulfonic acid groups.

The commercially available strongly acidic cation exchangers are known under the trade names Lewatit® (Lanxess), Purolite® (The Purolite Company), Dowex® (Dow Chemical Company), Amberlite® (Rohm and Haas Company), Amberlyst™ (Rohm and Haas Company).

Strongly acidic cation exchangers preferred according to the invention that may be mentioned are, for example, Lewatit® K 1221, Lewatit® K 1461, Lewatit® K 2431, Lewatit® K 2620, Lewatit® K 2621, Lewatit® K 2629, Lewatit® K 2649, Amberlite® IR 120, Amberlyst™ 131, Amberlyst™ 15, Amberlyst™ 31, Amberlyst™ 35, Amberlyst™ 36, Amberlyst™ 39, Amberlyst™ 46, Amberlyst™ 70, Purolite® SGC650, Purolite® C100H, Purolite® C150H, Dowex® 50×8, Serdolit® red and Nafion® NR-50.

Within the scope of one preferred embodiment, the reaction of isoprenol with the selected aldehyde of the formula (III) to be carried out according to the invention is carried out in the presence of at least one strongly acidic cation exchanger which is selected from the group of cation exchangers comprising Lewatit® K 1221, Lewatit® K 2629, Amberlyst™ 131, Purolite® SGC650, Purolite® C100H, Purolite® C150H, Amberlite® IR 120 and Dowex® 50×8.

Strongly acidic cation exchangers that are particularly preferred according to the invention are the cation exchangers Amberlyst™ 131 and/or Lewatit® K 1221.

A strongly acidic cation exchanger that is very particularly preferred according to the invention is Amberlyst™ 131, which, like the other specified cation exchangers, is commercially available.

To carry out the reaction according to the invention of isoprenol with the aldehyde of the formula (III), the specified starting materials and the selected amount of water, preferably in the form of a mixture, are brought into contact with the selected strongly acidic cation exchanger. The amount of cation exchanger to be used is not critical and can be freely chosen within wide limits taking into consideration the cost and processing aspects. The reaction can accordingly be carried out either in the presence of catalytic amounts, or else in the presence of large excesses, of the selected strongly acidic cation exchanger. Usually, the selected cation exchanger is used in an amount from about 5 to about 40% by weight, preferably in an amount of from about 20 to about 40% by weight and particularly preferably in an amount of from about 20 to about 30% by weight, in each case based on the sum of isoprenol used and aldehyde of the formula (III). Here, the data refer to the ready-to-use cation exchanger, which is usually pretreated with water and accordingly can comprise amounts of up to about 70% by weight, preferably from about 30 to about 65% by weight and particularly preferably from about 40 to about 65% by weight, of water. Particularly in the case of a discontinuous procedure, an addition of water beyond this may therefore be unnecessary when carrying out the process according to the invention.

The specified strongly acidic cation exchangers can be used either individually or in the form of mixtures with one another in the course of the process according to the invention.

The reaction to be carried out according to the invention can, if desired, also be carried out in the presence of a solvent that is inert under the reaction conditions, such as, for example, tert-butyl methyl ether, cyclohexane, toluene, hexane or xylene. The specified solvents can be used on their own or in the form of mixtures with one another. Within the context of one preferred embodiment of the process according to the invention, the reaction of isoprenol with the selected aldehyde of the formula (III) is carried out without addition of an organic solvent.

The reaction of isoprenol with the selected aldehyde of the formula (III) to be carried out according to the invention in the presence of water and in the presence of a strongly acidic cation exchanger is usually carried out at a temperature in the range from 0 to 60° C., preferably at a temperature in the range from 20 to 60° C. and particularly preferably at a temperature in the range from 20 to 50° C., where the temperature refers to that of the reaction mixture.

The reaction to be carried out according to the invention can, if desired, be carried out discontinuously or continuously. Here, for example in the discontinuous case, the reaction can be undertaken such that a mixture of isoprenol, the selected aldehyde of the formula (III) and water is introduced as initial charge in a suitable reaction vessel and the strongly acidic cation exchanger is added. Following conclusion of the reaction, the cation exchanger can then be separated off from the resulting reaction mixture by suitable separation methods, preferably by filtration or by centrifugation. The order in which the individual reaction components are brought into contact is not critical and can be varied according to the particular processing embodiment.

Within the context of one preferred embodiment, the reaction of isoprenol with the selected aldehyde of the formula (III) to be carried out according to the invention is carried out continuously. For this, for example a mixture of the starting materials isoprenol and aldehyde of the formula (III) to be reacted can be prepared with water and this mixture can be continuously brought into contact with a strongly acidic cation exchanger. For this, the selected cation exchanger can be introduced, for example, into a suitable flow reactor, for example a stirred reactor with inlet and outlet or a tubular reactor, and the starting materials and the water can be discharged continuously into this and the reaction mixture can be continuously discharged. In this connection, the starting materials and the water can, if desired, be introduced into the flow reactor as individual components or else in the form of a mixture as described above.

One preferred embodiment of the process according to the invention accordingly relates to a continuous process for the preparation and isolation of 2-substituted 4-hydroxy-4-methyltetrahydropyrans of the formula (I), comprising the steps a. providing a flow reactor comprising the selected strongly acidic cation exchanger;
b. continuously introducing isoprenol, the aldehyde of the formula (III) and water into the flow reactor;
c. continuously bringing isoprenol, the aldehyde of the formula (III) and water into contact with the strongly acidic cation exchanger in the flow reactor to give a reaction mixture comprising the desired 2-substituted 4-hydroxy-4-methyltetrahydropyrans;
d. continuously discharging the reaction mixture from the flow reactor, and
e. isolating and/or distillatively separating in a dividing wall column or in an interconnection of two distillation columns in the form of a thermal coupling and one or more side take-off points at an absolute operating pressure of up to 500 mbar, preferably from 3 to 200 mbar.

The process according to the invention permits the preparation and isolation of 2-substituted 4-hydroxy-4-methyltetrahydropyrans of the formula (I), specifically the preparation and isolation of 2-isobutyl-4-hydroxy-4-methyltetrahydropyrans of the formula (I). These are usually produced in the form of reaction mixtures which, besides the desired target compounds, can also comprise residues of the starting materials used, the water used and possibly, to a slight extent, also the dehydrated by-products of the formulae (IVa), (IVb) and/or (IVc)

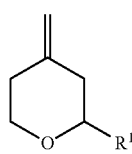

(IVa)

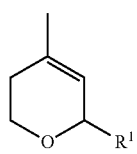

(IVb)

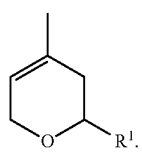

(IVc)

The process according to the invention permits the preparation and isolation of the desired hydroxypyrans of the formula (I) or preferably of 2-isobutyl-4-hydroxy-4-methyltetrahydropyrans of the formula (Ia) in high yield and high purity, where the undesired dehydration products of the formulae (Iva) to (IVc) are only produced to a minor extent, if at all.

Further possible by-products which may be mentioned are the acetals of the formula (V)

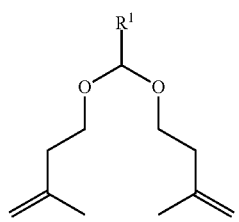

(V)

and the 1,3-dioxanes of the formula (VI)

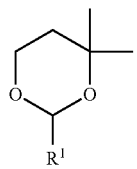

(VI)

where in the case of the reaction of isoprenol with isovaleraldehyde preferred according to the invention, the radical $R^1$ is in each case isobutyl (corresponding to the compounds of the formula (Va) or (VIa)). Just like the unreacted starting compounds and/or the starting compounds used in excess, these by-products can be advantageously returned again to the reaction.

The reaction mixtures obtained according to the invention typically consist to an extent of about 50 to about 90% by weight, often to about 60 to about 80% by weight, of the desired 2-substituted 4-hydroxy-4-methyltetrahydropyrans of the formula (I) and only up to about 20% by weight, preferably only up to about 15% by weight and particularly preferably only up to 10% by weight, of the dehydration products of the formulae (IVa) to (IVc), in each case based on the total weight of the crude product obtained and moreover of the unreacted starting materials and/or starting materials used in excess, and also the other specified by-products.

One preferred embodiment of the process according to the invention relates to the preparation and isolation of 2-substituted 4-hydroxy-4-methyltetrahydropyrans in the form of mixtures of the cis-diastereomers of the formula (Ic)

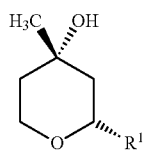

(Ic)

and of the trans-diastereomers of the formula (Id)

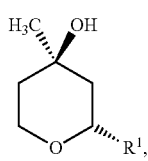
(Id)

where the diastereomer ratio of the cis-diastereomer of the formula (Ic) to the trans-diastereomer of the formula (Id) is 65:35 to 95:5, preferably 70:30 to 85:15, and $R^1$ has the meaning given above, in particular the preferred meanings.

In particular for the reaction of isoprenol with isovaleraldehyde preferred according to the invention, in the course of the process according to the invention 2-isobutyl-4-hydroxy-4-methyltetrahydropyran is obtained in the form of mixtures of the cis-diastereomer of the formula (Ie)

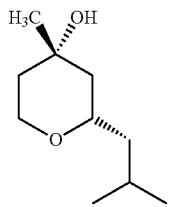
(Ie)

and of the trans-diastereomers of the formula (If)

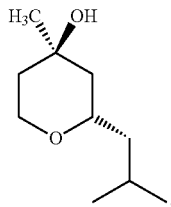
(If)

where the diastereomer ratio of the cis-diastereomer of the formula (Ie) to the trans-diastereomer of the formula (If) is 65:35 to 95:5, preferably 70:30 to 85:15. On account of their particular olfactory properties, mixtures of this type are suitable to a considerable degree for use as aroma chemicals, for example as component with lily of the valley scent for producing fragrance compositions.

The object of the invention is also to indicate a process with which stereoisomeric alcohols of the formula (I) can be isolated from a crude mixture with low capital and energy requirement.

According to the invention, this object is achieved by a process for the isolation of two stereoisomeric alcohols of the formula (I) from a crude mixture by rectification, where the crude mixture is introduced into a feed column at the side, at least one take-off column coupled to the feed column is provided and a first alcohol of the formula (I) and a second alcohol of the formula (I) are drawn off from the take-off column(s), where the feed column and the take-off columns are coupled such that at least in the region of the take-off of the alcohols, no crossmixing of vapors and condensate between feed column and take-off column(s) takes place.

The feed column and discharge column(s) are "coupled", i.e. joined together such that mass transfer is possible between them. To avoid cross mixing of vapors or condensate between the feed column and the discharge column(s) in the region of the take-off of the alcohols, the columns are coupled such that there is no "straight-line" route from the feed point to the take-off points, rather each route from the feed point to the take-off points comprises an "ascending" and a "descending" section (in any desired order), i.e. the transfer of condensate and/or vapors between these points can take place essentially only through evaporation/condensation or condensation/evaporation.

Preferably, at least one of the alcohols, in particular both the first and also the second alcohol, is removed at a side take-off of a take-off column.

The procedure is preferably one in which
a) the crude mixture is introduced into a feed column with rectifying section positioned above the feed point and stripping section positioned below the feed point,
b) an upper combining column communicating with the upper end of the rectifying section and with a condenser at the top of the column, and a lower combining column communicating with the lower end of the stripping section and having a heater at the bottom are provided,
c) a take-off column communicating with the upper combining column and the lower combining column is provided which has two side take-offs arranged in the longitudinal expansion of the take-off column at a distance from one another,
d) the first alcohol is drawn off at the upper side take-off and the second alcohol is drawn off at the lower side take-off, and
e) low-boiling components are drawn off at the top or in the upper region of the upper combining column, and high-boiling components are drawn off in the bottom of the lower combining column.

The feed column, take-off column, upper combining column and lower combining column can be discrete structural elements or be configured as part or chamber of a distillation column which combines several functions. The expression "communicating columns" means that there is a transfer both of ascending vapors and also of discharging condensate between them.

In one preferred embodiment, a so-called dividing wall column is used for the distillation, i.e. the feed column and the take-off column are designed as part chambers open on both sides to in each case one combining space which extend over a section of the longitudinal expansion of a distillation column, and are separated from one another by a dividing wall. The dividing wall can be integrated into the column in a fixed manner, e.g. welded in, or else it is attached in the column in a removable manner, e.g. inserted. The removable fixing offers advantages, such as greater flexibility, simpler packing of the column with internals and low capital costs.

In alternative embodiments, thermally coupled columns are used for the distillation, e.g. a distillation column with a thermally coupled precolumn or a distillation column with a thermally coupled aftercolumn. Distillation columns with connected auxiliary columns are known per se and familiar to the person skilled in the art.

The stereoisomeric alcohols in the process according to the invention are the alcohols of the formula (I), in particular those of the formulae (Ic) and (Id) or very particularly preferably those of the formulae (Ie) and (If). In a particularly preferred embodiment, the first alcohol is compounds of the formula (Ie), the second alcohol is the compound of the formula (If). A corresponding crude mixture can be prepared for example in the case of the synthesis stated above of tetrahydropyranols of the formula (I) substituted in the 2 position by reacting components (II) and (III) in the presence of a strongly acidic ion exchanger.

The crude mixture typically comprises 15 to 20% by weight of the trans-pyranol of the formula (If); 45 to 65% by weight of the cis-pyranol of the formula (Ie); 10 to 20% by weight of compounds boiling lower than the first alcohol; 1 to 3% by weight of compounds boiling higher than the second alcohol; the crude mixture is preferably essentially free from compounds which boil between the first and second alcohols.

The process according to the invention is illustrated in more detail below by reference to the preferred embodiment using a dividing wall column with two liquid side take-offs. All of the statements apply accordingly for alternative column arrangements, such as thermally coupled columns.

The pressure at the top of the column at the top of which the compounds boiling lower than the first alcohol are drawn off, in particular the upper combining column, is preferably up to 400 mbar, preferably 3 to 200 mbar, particularly preferably 3 to 100 mbar, and very particularly preferably 4 to 60 mbar.

One preferred embodiment of the process according to the invention is one wherein the feed column and the take-off column are designed as part chambers open on both sides to in each case one combining space which extend over a section of the longitudinal expansion of a distillation column, and are separated from one another by a dividing wall.

The sum of theoretical plates of upper combining column, feed column, take-off column and lower combining column is preferably 30 to 110, in particular 40 to 90.

Preferably, the upper combining column is apportioned 5 to 50%, in particular 15 to 30%, the rectifying section of the feed column is apportioned 5 to 50%, in particular 15 to 30%, the stripping section of the feed column is apportioned 5 to 50%, in particular 15 to 40%, the part of the take-off column positioned above the upper side take-off is apportioned 5 to 50%, in particular 15 to 30%, the part of the take-off column positioned between the side take-offs is apportioned 5 to 50%, in particular 15 to 30%, the part of the take-off column positioned below the lower side take-off is apportioned 5 to 50%, in particular 15 to 40%, and the lower combining column is apportioned 5 to 50%, in particular 15 to 30%, of the sum of theoretical plates of upper combining column, feed column, take-off column and lower combining column.

Preferably, the ratio of the sum of theoretical plates of the feed column to the sum of theoretical plates of the take-off column is 0.8 to 1.1, in particular 0.9 to 1.0.

The feed column, the upper combining column, the lower combining column and the take-off column preferably comprise separation-efficient internals, such as trays, structured packings, e.g. sheet-metal or fabric packings such as Sulzer Meltallapak, Sulzer BX, Montz B1 or Montz A3 or Kühni Rhombopak, or random beds of packings, such as e.g. Dixon rings, Raschig rings, high-flow rings or Raschig super-rings. It is preferred that at least the feed column and/or take-off column are provided entirely or in sections with structured packings. Structured packings, preferably sheet-metal or fabric packings, with a specific surface area of from 100 to 750 $m^2/m^3$, in particular 250 to 500 $m^2/m^3$, have proven to be particularly useful. They permit high separation efficiencies coupled with low pressure drops.

One preferred embodiment of the process according to the invention is one wherein the feed column and/or take-off column are provided entirely or in sections with structured packings or random packings.

When using a dividing wall column, it has proven favorable if the dividing wall is designed to be thermally insulating at least in one section, e.g. is filled in jacketed form with gas space in between. A description of the different options for thermal insulation of the dividing wall can be found in EP-A 640 367.

The crude mixture is preferably introduced into the feed column in a rate-controlled manner, for example by conveying it by means of a controllable pump or introducing it above an adequate static feed height of e.g. at least one meter via a controllable valve. Expediently, a minimum feed amount is provided which must not be fallen below and which is e.g. 30% below the normal value for which the plant is designed.

It may sometimes be advantageous to evaporate the crude mixture beforehand and to introduce it into the feed column partially or completely in vapor form. The partially preevaporated crude mixture is then introduced into the feed column as a two-phase stream or in the form of one liquid and one vaporous stream. The preevaporation is suitable if the crude mixture comprises relatively large amounts of low-boiling components. The preevaporation can deburden the stripping section of the feed column.

It is preferred to remove the side take-offs in liquid form. The take-off of the first alcohol is preferably regulated via measurement values of the temperature at a point in the take-off column positioned between the upper end of the take-off column and the upper side take-off and which is preferably 3 to 8, in particular 4 to 6, theoretical plates below the upper end of the take-off column. The amount drawn off is increased with increasing temperature, and vice versa. Expediently, the take-off is limited such that the amount of condensate which runs to the section of the take-off column positioned between the side take-offs does not drop below a minimum value which must not be fallen below and which is e.g. 30% below the normal value for which the plant is designed.

One preferred embodiment of the process according to the invention is one in which first alcohol and the second alcohol are drawn off in liquid form at the side take-offs of the dividing wall column.

The take-off of the second alcohol is preferably regulated via measurement values for the liquid level in the heater. The amount drawn off is increased with increasing liquid level, and vice versa.

The reflux ratio of the condenser is preferably regulated by measurement values for the temperature at a point in the region of the upper combining column which is preferably arranged 3 to 8, in particular 4 to 6, theoretical plates below the upper end. Of course, instead of the reflux ratio, it is also possible to regulate the amount of distillate removed, i.e. the take-off of the low-boiling components, as a result of which the reflux ratio is regulated indirectly.

The removal of high-boiling components from the bottom is preferably regulated via measurement values for the temperature at a point in the region of the lower combining column which is positioned preferably 3 to 8, in particular 4 to 6, theoretical plates above the lower end.

The heating output of the heater is suitably regulated by the pressure difference between a point at the upper end of the upper combining column and a point at the lower end of the lower combining column.

The vapor stream from the lower combining column is divided between the feed column and the take-off column preferably in a ratio of 0.8:1.2, in particular 0.9:1.1. A certain division ratio is established e.g. by changing the relative cross section of the feed column and take-off column, through selection and/or dimensioning of the separation-efficient internals and/or the incorporation of devices generating a pressure drop, such as diaphragms.

The condensate stream from the upper combining column is divided between the feed column and the take-off column preferably in a ratio of 0.1:1.0, in particular 0.3:0.6.

To remove or divide condensate at a point in a column, e.g. to divide the condensate from the upper combining column between the feed column and take-off column or to remove liquid side take-offs, the condensate is suitably fed to collecting containers arranged inside or outside the column. The collecting containers serve as pump receiver or provide a sufficiently high static liquid level which permits liquid removal or division regulated by control elements, for example valves. When using packed columns, collecting trays are expediently provided, from which the condensate is passed to the collecting containers.

During the distillative purification by isolation of the alcohols of the formulae (Ie) and (If) from crude mixtures, the fraction obtained should comprise, besides the desired compound, the lowest possible fraction of impurities with higher or lower boiling points. Depending on the intended use, the specifications as regards the maximum permissible content of compounds with higher or lower boiling points are different. As a rule, individual components critical for the separation problem are specified, in most cases those with a narrow boiling point difference with respect to the desired compound or those whose presence, even in low concentrations, is particularly troublesome, so-called key compounds, or the sum of two or more key compounds.

Compliance with the specification for the concentration of compounds boiling higher than the first alcohol (including the second alcohol) in the first alcohol pure fraction is regulated in the process according to the invention preferably via the division ratio of the condensate stream from the upper combining column. When using a dividing wall column this is the division ratio of the liquid at the upper end of the dividing wall. For this, in the region of the upper combining column, preferably at its lower end, measurement values are obtained for the concentration of at least one compound boiling higher than the first alcohol and these measurement values are used to form control interventions for the division ratio of the condensate stream from the upper combining column into the feed column and the take-off column. With increasing concentrations of compounds with higher boiling points, an increasingly larger fraction of the condensate is passed to the feed column. The concentration of compounds boiling higher than the first alcohol at the lower end of the upper combining column should be 10 to 80%, preferably 30 to 50%, of the maximum permissible value of the concentration of these compounds in the first alcohol pure fraction.

Compliance with the specification for the concentration of compounds boiling lower than the second alcohol (including the first alcohol) in the second alcohol pure fraction is regulated in the process according to the invention preferably via the heating output of the heater. For this, in the region of the lower combining column, preferably at its upper end, measurement values for the concentration of at least one compound boiling lower than the second alcohol are obtained and these measurement values are used to form control interventions for the heating output of the heater. With increasing concentration of lower boiling compounds, the heating output is increased, and vice versa. The concentration of compounds boiling lower than the second alcohol at the upper end of the lower combining column should be 10 to 80%, preferably 30 to 50%, of the maximum permissible value of the concentration of these compounds in the second alcohol pure fraction.

In order to obtain measurement values for the concentration of the key compounds discussed above, gaseous or liquid samples can be removed continuously or periodically at the respective point and investigated as regards their composition, preferably by gas chromatography. For sample removal, suitable sample removal sites are preferably provided in the distillation columns, via which lances can be introduced into the columns. In many cases, an adequate statement about the composition of the vapors and/or of the condensate at a point in a distillation column can also be made by reference to a simple temperature measurement if the correlation of the temperature profile with the mixture composition is known or has been determined beforehand.

During the distillation of fragrances in successive columns in which the components are drawn off overhead in the order of their volatility, the thermal stress may, on account of the high residence times in the column bottoms, lead to product impairment and/or to the formation of undesired odor carriers. This may lead to the resulting pure product being outside of the required specification and/or not passing the olfactory test. The process according to the invention minimizes the thermal stress of the mixture to be separated and circumvents the disadvantages associated therewith.

The various embodiments of thermally coupled distillation columns and of dividing wall columns are known in the literature, e.g. DEA-102 23 971.

The examples below serve to illustrate the invention without limiting it in any way:

Gas chromatographic analyses were carried out according to the following method: 30 m DB-WAX, ID.: 0.32 mm, FD.: 0.25 μm; 50° C., 3° C./min—170° C., 20° C./min to 230° C.—17 min; Inj. 200° C., Det. 280° C., $t_R$=min; $t_R$ (isovaleraldehyde): 4.1; $t_R$ (dihydropyran isomers of the formulae (IVa) to (IVc)): 10.0; 11.8; 12.3; $t_R$ (isoprenol): 10.6; $t_R$ (1,3-dioxane (Va)): 12.1; $t_R$ (acetal (VIa)); 24.1; $t_R$ (trans-pyranol of the formula (Ie)): 28.2; $t_R$ (cis-pyranol of the formula (Id)): 29.8. Concentrations of the crude products obtained (% by weight) were determined by means of GC analysis using an internal standard.

The water content of the crude products obtained was determined by means of Karl-Fischer titration.

Example 1

An apparatus consisting of a jacketed glass tubular reactor with an internal diameter of 2 cm and a length of 36 cm was filled with 50 g of the strongly acidic cation exchanger Amberlyst™ 131. Prior to use, the cation exchanger was firstly washed several times with water, then once with methanol and finally washed free of methanol using water.

The jacketed glass reactor was filled with a mixture of isovaleraldehyde (112.5 g, 1.31 mol), isoprenol (125 g, 1.45 mol) and 12.5 g of water at room temperature. The reaction solution was circulated for 4 h at a temperature of 35° C. with a circulation volume of 490 ml/h. The reaction solution was then circulated for a further 10 h at a temperature of 40° C. with a circulation volume of 490 ml/h. The jacketed glass reactor was operated at a temperature of 35-40° C. This gave a crude product in an amount of 247.2 g (yield with regard to cis/trans-pyranol (Ie and If) 74%) with the following composition:

isovaleraldehyde: 0.53 GC % by weight, isoprenol: 1.23 GC % by weight, dihydropyran isomers (IVa-c): 8.96 GC % by weight 1,3-dioxane (Va): 8.84 GC % by weight, acetal (VIa): 0.49 GC % by weight, trans-pyranol (If): 18.34 GC % by weight,
cis-pyranol (Ie): 49.27 GC % by weight,
water: 6.0%

Example 2

The jacketed glass reactor was filled with a mixture of isovaleraldehyde (77.4 g, 0.9 mol), isoprenol (86.1 g, 1.0 mol) and 8.6 g of water at room temperature. The reaction solution was circulated for 10 h at a temperature of 25° C. with a circulation volume of 1.5 l/h. The jacketed glass reactor was heated to 25° C. This gave a crude product in an amount of 169.4 g (yield with regard to cis/trans-pyranol (Ie and If) 79%) with the following composition:
isovaleraldehyde: 0.44 GC area %,
isoprenol: 3.57 GC area %,
dihydropyran isomers (IVa-c): 9.76 GC area %,
1,3-dioxane (Va): 3.16 GC area %,
acetal (VIa): 0.99 GC area %,
trans-pyranol (If): 18.91 GC % by weight,
cis-pyranol (Ie): 54.13 GC % by weight,
water 6.9%

Example 3

Distillation by Means of Two Laboratory Columns

The first column was constructed of two jacketed, internally mirrored and evacuated glass sections (top 800 mm long; bottom 640 mm) with an internal diameter of 43 mm. The internals were Montz A3-750 metal sheet packings. The separation efficiency of the column corresponds to about 15 theoretical plates.

The column was heated using an oil-heated laboratory rotary thin-film evaporator. At the top of the column, the vapors were condensed using a glass condenser chilled with cooling water. For the separation of the two phases of the top condensate, a glass phase separator was incorporated. The lower aqueous phase was driven out in a level-controlled manner. The upper organic phase was divided with the help of a reflux divider in a fixed ratio. One part was driven off as top product. The other part was placed onto the fabric packing at the top.

Temperatures at different heights in the column and also the top pressure and the pressure drop over the column were measured by means of a measurement recording system. The column had flow meters in the inlets and outlets, and a return flow meter, the measurement of which served as the control parameter for the inlet temperature of the oil thermostat. This control system ensured a constant return rate, which also established a constant pressure difference. The feed to the column took place between the two column sections. The feed stream was run in at room temperature. The flow rate was 995 g/h. The mixture had the following composition:
7.3% of water (Karl-Fischer method)
0.79 GC % by weight of isovaleraldehyde
3.2 GC % by weight of isoprenol
7.4 GC % by weight of dihydropyran isomers (IVa-c)
6.0 GC % by weight of 1,3-dioxane (Va)
0.36 GC % by weight of acetal (VIa)
18.0 GC % by weight of trans-pyranol (If)
52.3 GC % by weight of cis-pyranol (Ie)

The column was operated at a top pressure of 50 mbar and a return rate of 270 g/h. Here, a pressure drop of ca. 2.5 mbar was established. At the top of the column, a temperature of 62° C. was measured, and in the bottom a temperature of 130° C. was measured. By means of a balance control system, the bottom take-off amount was fixed at 785 g/h. The top take-off amount was 130 g/h.

Gas chromatographic analyses were carried out according to the following method: 30 m DB-WAX, ID.: 0.32 mm, FD.: 0.25 μm; 50° C., 3° C./min—170° C., 20° C./min to 230° C.—17 min; Inj. 200° C., det. 280° C., $t_R$=min; $t_R$ (isovaleraldehyde): 4.1; $t_R$ (dihydropyran isomers of the formulae (IVa) to (IVc)): 10.0; 11.8; 12.3; $t_R$ (isoprenol): 10.6; $t_R$ (1,3-dioxane (Va)): 12.1; $t_R$ (acetal (VIa)): 24.1; $t_R$ (trans-pyranol of the formula (If)): 28.2; $t_R$ (cis-pyranol of the formula (Ie): 29.8. Concentrations of the resulting crude products (% by weight) were determined by GC analysis by means of an internal standard.

The top stream drawn off from the phase separator at the top of the column comprised:
2.5% of water (Karl-Fischer method)
4.6 GC area % of isovaleraldehyde
40.5 GC area % of dihydropyran isomers (IVa-c)
23.9 GC area % of isoprenol
28.1 GC area % of 1,3-dioxane (Va)

In the bottom take-off the following were determined:
0.03% of water (Karl-Fischer method), and by GC analysis
3.1 GC % by weight of dihydropyran isomers (IVa-c)
2.6 GC % by weight of 1,3-dioxane (Va)
22.4 GC % by weight of trans-pyranol (If)
65.6 GC % by weight of cis-pyranol (Ie).

The distillation yield with regard to cis- and trans-pyranol (Ie and If) was 100%.

The second laboratory column was constructed as a dividing wall column. It was constructed of three jacketed, internally mirrored and evacuated glass sections with an internal diameter of 43 mm. The middle column section with a total length of 105 cm was provided with a firmly welded-in dividing wall made of glass about 1 mm in thickness. In the region of the dividing wall, the column is equipped with 1 m of Montz A3 1000 packing on the feed side and 0.9 m of Montz A3 1000 packing on the removal side. Above and below the dividing wall, glass sections 50 cm in length were used, each of which was equipped with 33 cm of Sulzer DX packings. The separation efficiency in the dividing wall region was ca. 32 theoretical plates. The total number of theoretical plates including the dividing wall region was ca. 50.

The column was heated using an oil-heated laboratory rotary thin-film evaporator. At the top of the column, the vapors were condensed using a glass condenser chilled with cooling water.

Temperatures at different levels in the column and the top pressure and the pressure drop over the column were measured by means of a measurement recording system. The column had flow meters in the inlets and outlets, and a return flow meter, the measurement of which served as the control parameter for the inlet temperature of the oil thermostat. This control system ensured a constant return rate, which also established a constant pressure difference. The division of the amount of liquid above the dividing wall between feed section and withdrawal section of the dividing wall was achieved by means of a swivel funnel on a time cycle.

The feed was added at the height of the middle of the dividing wall section. The feed stream used was the mixture from the bottom discharge of the first column. The feed rate was 300 g/h.

The column was operated at a top pressure of 10 mbar and a return rate of 400 g/h. Here, a pressure drop of about 1.5 mbar was established. At the top of the column, a temperature of 78° C. was measured, and in the bottom a temperature of 127° C. (±0.5 K). By means of a balance control system, the bottom take-off was fixed at 14 g/h (±1 g/h) and the distillate withdrawal at 26 g/h (±1 g/h). The reflux ratio was thus about 15:1.

The liquid was divided above the dividing wall in a ratio of 1:2 (feed section: withdrawal section). At the side of the dividing wall opposite the feed side, at the same height as the feed stream, a liquid side take-off was removed. The flow rate was fixed at 260 g/h. The pure product obtained at the side take-off comprised
23.3 GC area % of trans-pyranol (If)
76.5 GC area % of cis-pyranol (Ie)
The top stream drawn off at the top of the column comprised:
0.25 GC % by weight of isovaleraldehyde
34.9 GC % by weight of dihydropyran isomers (IVa-c)
0.54 GC % by weight of isoprenol
28.5 GC % by weight of 1,3-dioxane (Va)
24.6 GC % by weight of trans-pyranol (If)
2.1 GC % by weight of cis-pyranol (Ie)
The stream drawn off at the bottom of the column comprised:
0.45 GC % by weight of trans-pyranol (If)
6.8 GC % by weight of cis-pyranol (Ie)
The distillation yield with regard to cis- and trans-pyranol (Ie and If) was ca. 90%.

Example 4

The first column had an identical structure to that used in example 3 and was operated in an identical manner.

The second laboratory column was constructed as a dividing wall column. It was constructed from 6 jacketed, internally mirrored and evacuated glass sections with an internal diameter of 43 mm. Column sections 2 and 3 (counted from the bottom) with a total length of 232 cm were provided with a firmly welded-in dividing wall made of glass about 1 mm in thickness. In the region of the dividing wall, the column is equipped with 0.6 m of Sulzer DX packing on the feed side and on the removal side. Above the dividing wall, two glass sections 60 cm in length and one glass section 30 cm in length were used which were equipped with in total 147 cm of Sulzer CY packings. Below the dividing wall, a glass section 100 cm in length was used, which was equipped with 64 cm of Sulzer CY packings. The separation efficiency in the dividing wall region was ca. 11 theoretical plates. The total number of theoretical plates including the dividing wall region was ca. 45.

The column was heated using an oil-heated laboratory rotary thin-film evaporator. At the top of the column, the vapors were condensed using a thermostat-cooled glass condenser.

Temperatures at different levels in the column and the top pressure and the pressure drop over the column were measured by means of a measurement recording system. The column had flow meters in the inlets and outlets, and a return flow meter, the measurement of which served as the control parameter for the inlet temperature of the oil thermostat. This control system ensured a constant return rate, which also established a constant pressure difference. The division of the amount of liquid above the dividing wall between feed section and withdrawal section of the dividing wall was achieved by means of a swivel funnel on a time cycle.

The feed was heated to 80° C. by means of an oil-heated glass heat exchanger and added at the height of the middle of the dividing wall section. The feed stream used was the mixture from the bottom discharge of the first column. The feed flow rate was 398 g/h.

The column was operated at a top pressure of 10 mbar and a return rate of 874 g/h. Here, a pressure drop of about 4.5 mbar was established. At the top of the column, a temperature of 96° C. was measured, and in the bottom a temperature of 120° C. (±0.5 K) was measured. By means of a balance control system, the bottom take-off was fixed at 32 g/h (±1 g/h) and the distillate withdrawal at 46 g/h (±1 g/h). The reflux ratio was thus about 19:1.

The liquid was divided above the dividing wall in a ratio of 1:2 (feed section: withdrawal section). At the side of the dividing wall opposite the feed side, at the same height as the feed stream, a liquid side take-off was removed. The flow rate was fixed at 319 g/h. The pure product obtained at the side take-off comprised:
22.1 GC % by weight of trans-pyranol (If)
77.0 GC % by weight of cis-pyranol (Ie)
The top stream drawn off at the top of the column comprised:
24.3 GC % by weight of dihydropyran isomers (IVa-c)
0.40 GC % by weight of isoprenol
18.3 GC % by weight of 1,3-dioxane (Va)
45.6 GC % by weight of trans-pyranol (If)
4.2 GC % by weight of cis-pyranol (Ie)
The stream drawn off at the bottom of the column comprised:
2.0 GC area % of trans-pyranol (If)
34.0 GC area % of cis-pyranol (Ie)
The distillation yield with regard to cis- and trans-pyranol (Ie and If) was ca. 90%.

The invention claimed is:

1. A process for the preparation of 2-substituted 4-hydroxy-4-methyltetrahydropyrans of the formula (I)

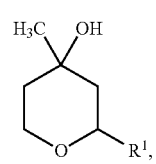

where the radical $R^1$ is a straight-chain or branched alkyl or alkenyl radical having 1 to 12 carbon atoms, an optionally alkyl-substituted cycloalkyl radical having in total 3 to 12 carbon atoms or an optionally alkyl- and/or alkoxy-substituted aryl radical having in total 6 to 12 carbon atoms, which comprises reacting 3-methylbut-3-en-1-ol of the formula (II)

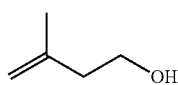

with an aldehyde of the formula (III)

where the radical $R^1$ has the same meaning as in formula (I) and where the reaction is carried out in the presence of at least 10 mol % water, wherein the amount of water is based on the amount of 3-methylbut-3-en-1-ol of the formula (II) if the 3-methylbut-3-en-1-ol is used in deficit or to the amount of aldehyde of the formula (III) if used in deficit or, in the case of equimolar reaction of the two starting materials, to the quantitative amount of one of the two, and in the presence of a strongly acidic cation exchanger, and then the distillative separation is carried out in a dividing wall column or in an interconnection of at least two distillation columns in the form of a thermal coupling and one or more side take-off points at an absolute operating pressure of up to 500 mbar.

2. The process according to claim 1, wherein the radical $R^1$ is a straight-chain or branched alkyl or alkenyl radical having 1 to 12 carbon atoms, or an optionally alkyl- and/or alkoxy-substituted aryl radical having in total 6 to 12 carbon atoms.

3. The process according to claim 1, wherein the radical $R^1$ is isobutyl.

4. The process according to claim 1, wherein the radical $R^1$ is phenyl.

5. The process according to claim 1, wherein isoprenol and the aldehyde of the formula (III) are used in a molar ratio of from 0.7:1 to 2:1.

6. The process according to claim 5, wherein isoprenol and the aldehyde of the formula (III) are used in a molar ratio of from 1:1 to 1.5:1.

7. The process according to claim 1, wherein the reaction is carried out in the presence of an at least equimolar amount of water, where the amount of water refers to the amount of the starting material isoprenol used, optionally in deficit, or to the aldehyde of the formula (III), or, in the case of the equimolar reaction of the two starting materials, to the quantitative amount of one of the two.

8. The process according to claim 1, wherein a strongly acidic cation exchanger comprising sulfonic acid groups is used.

9. The process according to claim 1, wherein at least one strongly acidic cation exchanger is used in the H(+) form, where the ion exchanger comprises a polymer backbone having sulfonic acid groups and is either gel-like or comprises macroporous resins.

10. The process according to claim 1, wherein the ion exchanger is based on a polystyrene backbone with sulfonic acid groups or on a perfluorinated ion exchange resin with sulfonic acid groups.

11. The process according to claim 1, wherein the reaction is carried out without the addition of an organic solvent.

12. The process according to claim 1, wherein the reaction is carried out at a temperature in the range from 20 to 60° C.

13. The process according to claim 1, wherein the reaction is carried out continuously.

14. The process according to claim 13, comprising
a. providing a flow reactor comprising the selected strongly acidic cation exchanger;
b. continuously introducing isoprenol, the aldehyde of the formula (III) and water into the flow reactor;
c. continuously bringing isoprenol, the aldehyde of the formula (III) and water into contact with the strongly acidic cation exchanger in the flow reactor to give a reaction mixture comprising the 2-substituted 4-hydroxy-4-methyltetrahydropyrans and
d. continuously discharging the reaction mixture from the flow reactor, and
e. isolating and/or distillatively separating in a dividing wall column or in an interconnection of two distillation columns in the form of a thermal coupling and one or more side take-off points at an absolute operating pressure of up to 500 mbar.

15. The process according to claim 14, wherein the pressure from 3 to 200 mbar.

16. The process according to claim 1 for the preparation of 2-substituted 4-hydroxy-4-methyltetrahydropyrans in the form of mixtures of the cis-diastereomers of the formula (Ic)

and of the trans-diastereomers of the formula (Id)

where the diastereomer ratio of the cis-diasteromer of the formula (Ic) to the trans-diastereomer of the formula (Id) is 65:35 to 95:5, and $R^1$ is a straight-chain or branched alkyl or alkenyl radical having 1 to 12 carbon atoms, an optionally alkyl-substituted cycloalkyl radical having in total 3 to 12 carbon atoms or an optionally alkyl- and/or alkoxy-substituted aryl radical having in total 6 to 12 carbon atoms.

17. The process according to claim 1 for the continuous isolation of two stereoisomeric alcohols of the formula (I) from a crude mixture by rectification, where the crude mixture is introduced into a feed column at the side, at least one take-off column coupled to the feed column is provided and a first alcohol of the formula (I) and a second alcohol of the formula (I) are drawn off from the take-off column(s), where the feed column and the take-off columns are coupled such that at least in the region of the take-off of the alcohols, no crossmixing of vapors and condensate between feed column and take-off column(s) takes place.

18. The process according to claim 17, further comprising
a. introducing the crude mixture into a feed column with rectifying section positioned above the feed point and stripping section positioned below the feed point,
b. providing an upper combining column communicating with the upper end of the rectifying section and with a condenser at the top of the column, and a lower combining column communicating with the lower end of the stripping section and having a heater at the bottom,
c. providing a take-off column communicating with the upper combining column and the lower combining column which has two side take-offs arranged in the longitudinal direction of the take-off column at a distance from one another,
d. drawing off the first alcohol at the upper side take-off and drawing off the second alcohol at the lower side take-off, and
e. drawing off low-boiling components at the top or in the upper region of the upper combining column, and drawing off high-boiling components in the bottom of the lower combining column.

19. The process according to claim 18, where the feed column and the take-off column are designed as part chambers open on both sides to in each case one combining space which extend over a section of the longitudinal expansion of a distillation column, and are separated from one another by a dividing wall.

20. The process according to claim 19, wherein the first alcohol and the second alcohol are drawn off in liquid form at the side take-offs of the dividing wall column.

21. The process according to claim 18, wherein the feed column and/or take-off column are provided entirely or in sections with structured packings or random packings.

22. The process according to claim 18, wherein the dividing wall is designed to be thermally insulating at least in one section.

23. The process according to claim 18, wherein the crude mixture is introduced into the feed column partially or completely in vapor form.

* * * * *